(12) United States Patent
Shuros et al.

(10) Patent No.: US 9,579,501 B2
(45) Date of Patent: Feb. 28, 2017

(54) HIS BUNDLE LEAD DELIVERY SYSTEM

(71) Applicant: Cardiac Pacemakers, Inc., St. Paul, MN (US)

(72) Inventors: Allan C. Shuros, St. Paul, MN (US); Bruce A. Tockman, Scandia, MN (US); G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 527 days.

(21) Appl. No.: 14/014,007

(22) Filed: Aug. 29, 2013

(65) Prior Publication Data

US 2014/0067036 A1 Mar. 6, 2014

Related U.S. Application Data

(60) Provisional application No. 61/695,170, filed on Aug. 30, 2012.

(51) Int. Cl.
*A61N 1/00* (2006.01)
*A61N 1/05* (2006.01)
(Continued)

(52) U.S. Cl.
CPC .............. *A61N 1/059* (2013.01); *A61N 1/0573* (2013.01); *A61N 1/0565* (2013.01); *A61N 1/362* (2013.01); *A61N 1/372* (2013.01)

(58) Field of Classification Search
CPC .... A61N 1/0565; A61N 1/0573; A61N 1/059; A61N 1/362; A61N 1/372
See application file for complete search history.

(56) References Cited

U.S. PATENT DOCUMENTS 6,122,552 A * 9/2000 Tockman ............... A61M 25/10
607/116
6,224,557 B1 5/2001 Ziel et al.
(Continued)

FOREIGN PATENT DOCUMENTS

CN 101528145 A 9/2009
CN 102281819 A 12/2011
(Continued)

OTHER PUBLICATIONS

Calvi, Valeria et al., "Incidence rate and predictors of permanent pacemaker implantation after transcatheter aortic valve implantation with self-expanding CoreValve prosthesis", Journal Interv Card Electrophysiol, Nov. 26, 2011, 7 pages.
(Continued)

*Primary Examiner* — Lindsey G Hankins
(74) *Attorney, Agent, or Firm* — Faegre Baker Daniels LLP

(57) ABSTRACT

Various embodiments concern implanting a lead to directly stimulate the bundle of His. Various embodiments can include introducing a curve of an outer guide catheter into the right ventricle, extending a curve of an inner guide catheter from a lumen of the outer guide catheter, extending a fixation element on a distal tip of an anchor wire from a lumen the inner guide catheter, and anchoring the anchor wire to target tissue within the right ventricle, the target tissue along the septal wall and proximate the tricuspid valve and the bundle of His. A distal tip of an implantable lead with a lumen can then be advanced over the anchor wire to the target tissue as the anchor wire guides the distal tip of the lead to the target tissue.

6 Claims, 7 Drawing Sheets

(51) Int. Cl.
   *A61N 1/362*   (2006.01)
   *A61N 1/372*   (2006.01)

(56) References Cited

U.S. PATENT DOCUMENTS

| | | |
|---|---|---|
| 2004/0006268 A1 | 1/2004 | Gilboa et al. |
| 2005/0096589 A1* | 5/2005 | Shachar .............. A61B 1/00158 604/95.01 |
| 2005/0124881 A1 | 6/2005 | Kanai et al. |
| 2006/0106445 A1* | 5/2006 | Woollett ................ A61N 1/056 607/122 |
| 2007/0112405 A1* | 5/2007 | Williams .......... A61M 25/0041 607/122 |
| 2007/0165916 A1 | 7/2007 | Cloutier et al. |
| 2008/0082136 A1 | 4/2008 | Gaudiani |
| 2008/0287803 A1 | 11/2008 | Li et al. |
| 2009/0259272 A1* | 10/2009 | Reddy ................. A61N 1/0573 607/28 |
| 2009/0264780 A1* | 10/2009 | Schilling ................ A61N 1/057 600/509 |

FOREIGN PATENT DOCUMENTS

| | | |
|---|---|---|
| EP | 2275170 A1 | 1/2011 |
| JP | 2006506211 A | 2/2006 |
| JP | 2010503449 A1 | 2/2010 |
| WO | WO2009135075 A1 | 11/2009 |

OTHER PUBLICATIONS

Fraccaro, Chiara et al., "Incidence, Predictors, and outcome of Conduction Disorders After Transcatheter Self-Expandable Aortic Valve Implantation", The American Journal of Cardiology, Mar. 1, 2011, vol. 107, pp. 747-754.

Partial Search Report issued in PCT/US2013/057381, mailed Jan. 24, 2014, 6 pages.

International Search Report and Written Opinion issued in PCT/US2013/057381, mailed Apr. 15, 2014, 17 pages.

International Preliminary Report on Patentability issued in PCT/US2013/057381, completed Mar. 3, 2015, 11 pages.

* cited by examiner

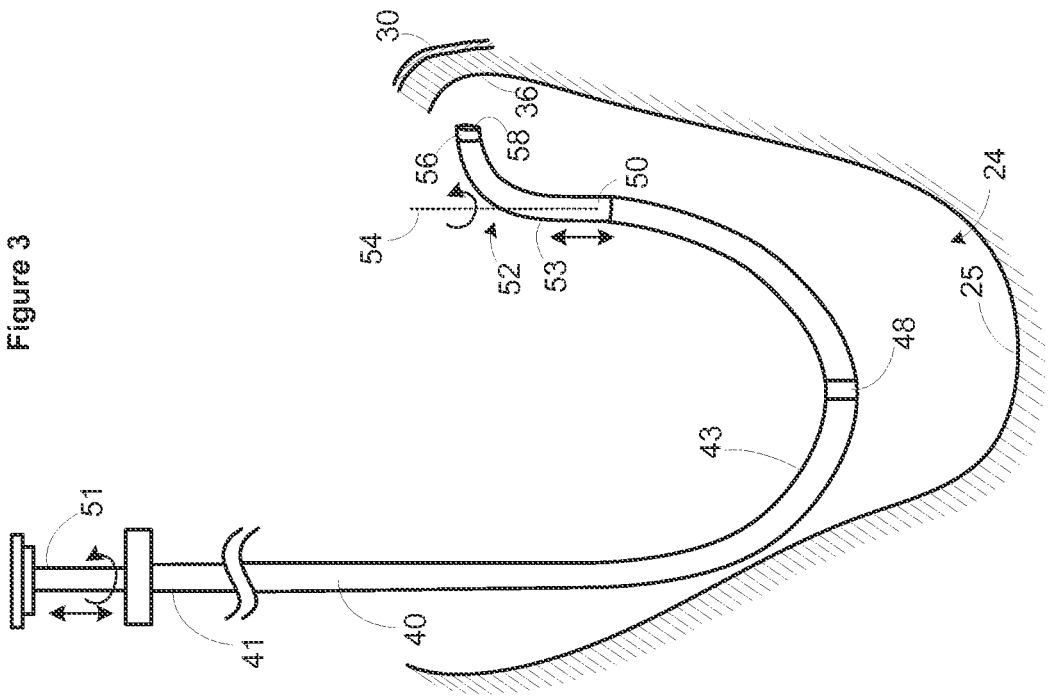
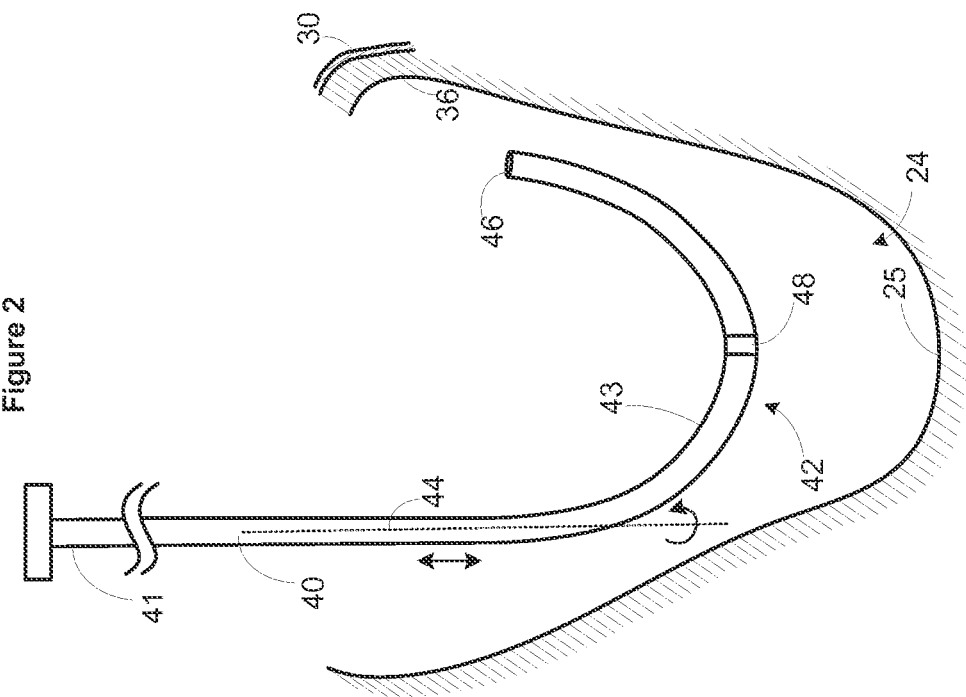

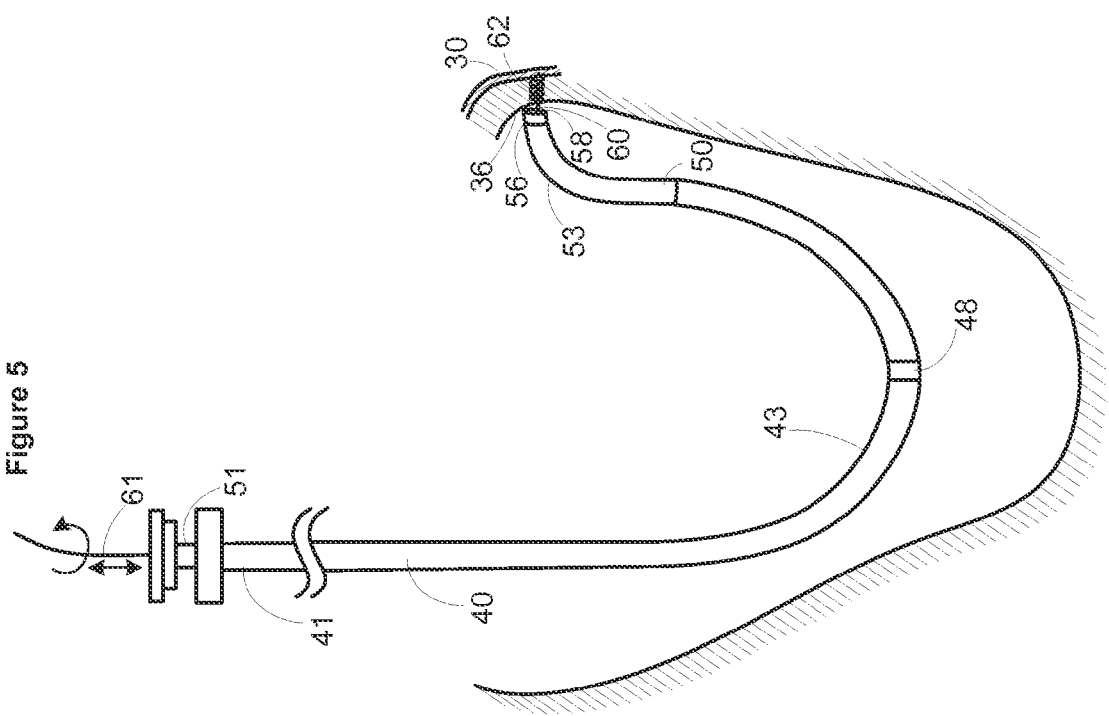
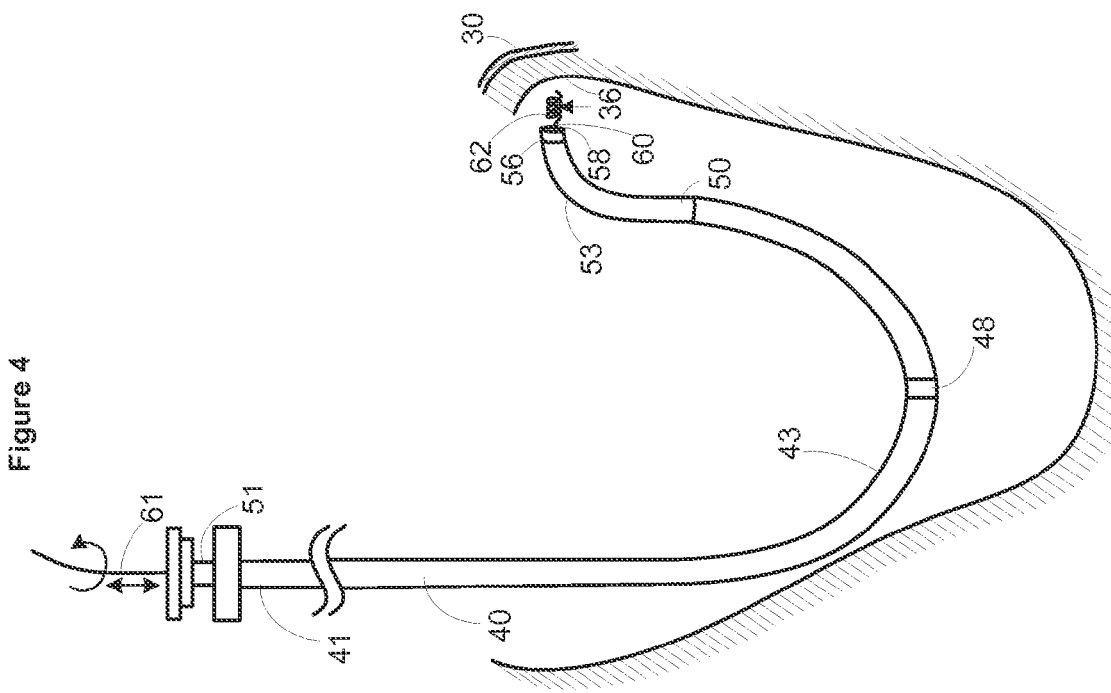

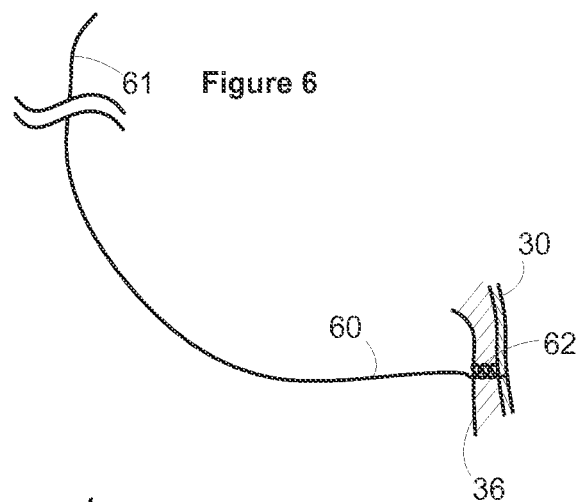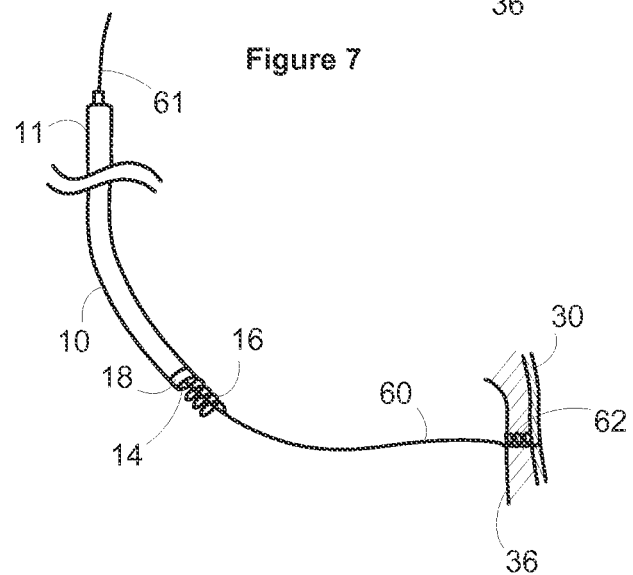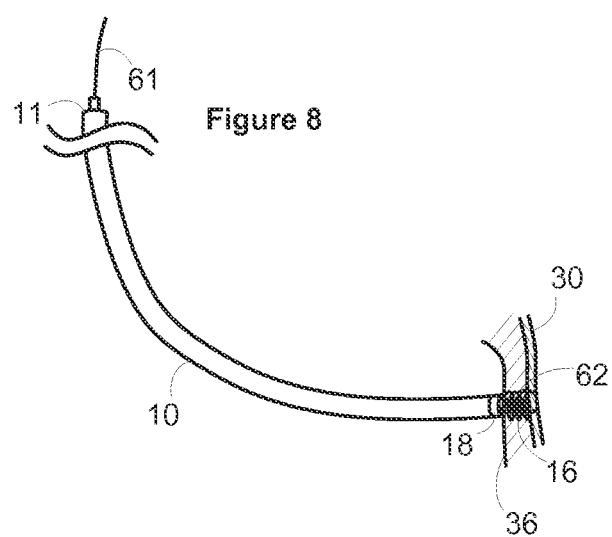

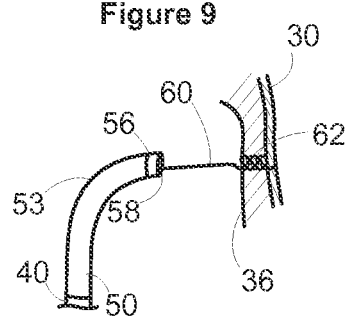
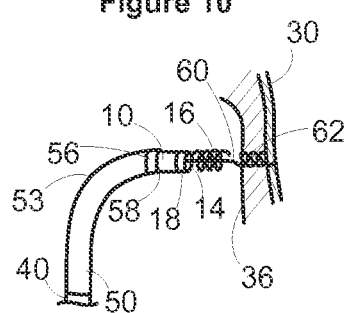
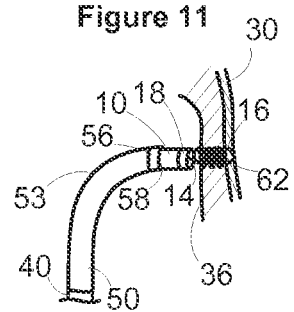

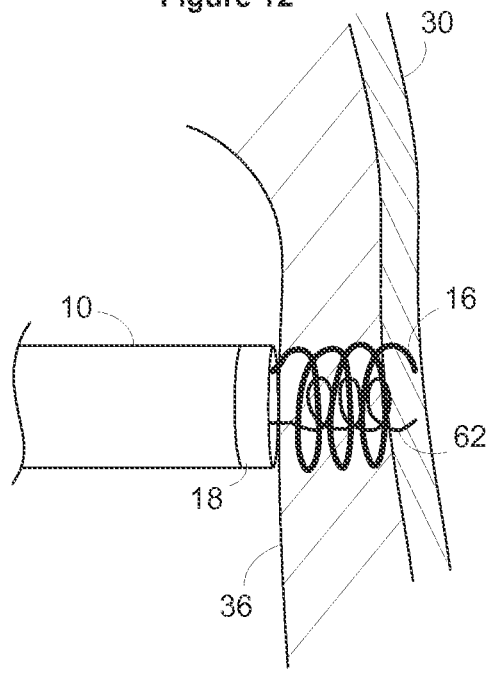
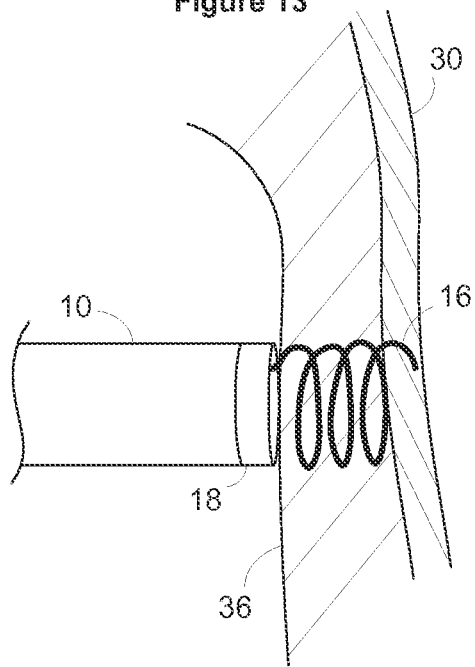

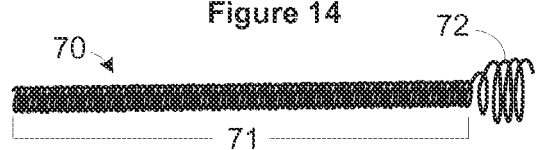
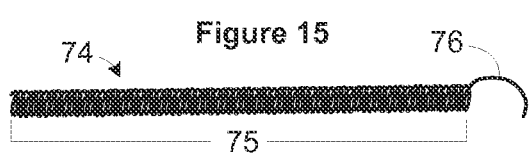
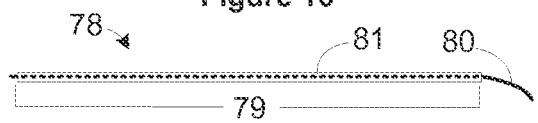
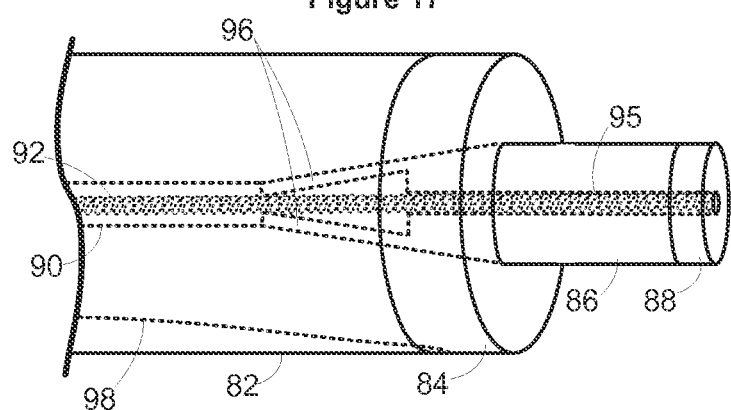
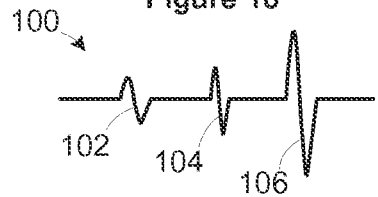

HIS BUNDLE LEAD DELIVERY SYSTEM

CROSS-REFERENCE TO RELATED APPLICATION

This application claims the benefit of U.S. Provisional Application No. 61/695,170, filed Aug. 30, 2012, which is incorporated herein by reference in its entirety.

TECHNICAL FIELD

The present disclosure relates to lead delivery systems. In particular, the present disclosure relates to delivery systems for stabilizing a lead for stimulation of the bundle of His from the right ventricle.

BACKGROUND

Cardiac rhythm management systems are useful for electrically stimulating a patient's heart to treat various cardiac arrhythmias. A proposed method of electrically stimulating the heart includes stimulating the bundle of His. By directly stimulating the bundle of His, both the right and left ventricles can be physiologically activated, potentially avoiding pacing induced dyssynchrony present with right ventricular apex pacing. There is a continuing need for improved delivery systems for targeting the bundle of His.

SUMMARY

In example 1, a system for delivering a lead to a target site, the system comprising: an outer guide catheter having a proximal end, a distal end having a distal tip, a lumen having an opening at the distal tip, and a preformed curve in the distal end of the outer guide catheter; an inner guide catheter having a proximal end, a distal end having a distal tip, a lumen having an opening at the distal tip, at least one electrode, and at least one conductor in electrical connection with the electrode and extending to the proximal end, the inner guide catheter moveable within the lumen of the outer guide catheter and extendable from the opening of the lumen at the distal tip of the outer guide catheter; an anchor wire having a proximal end, a distal end, and a fixation element on the distal end of the anchor wire, the anchor wire moveable within the lumen of the inner guide catheter and extendable from the opening of the lumen at the distal tip of the inner guide catheter, the anchor wire flexible, the fixation element configured to penetrate tissue of the target site to anchor the anchor wire to the tissue of the target site; and an implantable lead having a proximal end configured to interface with an implantable pulse generator, a distal end, at least one electrode on the distal end of the implantable lead, at least one conductor electrically connected to the at least one electrode and extending to the proximal end of the implantable lead, and a lumen sized to accommodate the anchor wire, the implantable lead flexible and configured to be advanced over the anchor wire to bring the at least one electrode of the implantable lead in contact with the target site while the anchor wire is anchored to the tissue of the target site and the anchor wire extends within the lumen of the implantable lead.

In example 2, the system of example 1, wherein the target site is the bundle of His, below the tricuspid valve, within the right ventricle.

In example 3, the system of either of example 1 or 2, wherein the curve in the distal end of the outer guide catheter is between 150 and 210 degrees.

In example 4, the system of any of examples 1-3, wherein the inner guide catheter comprises a curve along a distal end.

In example 5, the system of example 4, wherein the curve of the outer guide catheter is rotatable about a first axis of the outer guide catheter and the curve of the inner guide catheter is rotatable relative to the outer guide catheter about a second axis when the curve of the inner guide catheter extends beyond the opening of the lumen at the distal tip of the outer guide catheter, the first axis not parallel with the second axis.

In example 6, the system of any of examples 1-5, wherein the implantable lead further comprises a fixation element configured to penetrate the tissue of the target site and anchor the implantable lead to the tissue of the target site.

In example 7, the system of any of examples 1-6, wherein: the fixation element of the anchor wire is a first helix; the fixation element of the implantable lead is a second helix with lumen; and the first helix and the second helix are sized such that the first helix can be moved through the lumen of the second helix.

In example 8, the system of any of examples 1-7, wherein the anchor wire comprises: a conductor extending from the proximal end to the distal end of the anchor wire; and an electrical insulator that insulates the conductor from the proximal end to the distal end of the anchor wire, the fixation element electrically connected to the conductor and exposed to one or both of receive electrical energy from, and deliver electrical energy to, the tissue of the target site.

In example 9, the system of any of examples 1-8, wherein the outer guide catheter comprises an electrode on an exterior surface of the outer guide catheter along the curve of the outer guide catheter.

In example 10, the system of any of examples 1-9, wherein the electrode of the inner guide catheter and the fixation element of the anchor wire are electrically connected to circuitry configured to sense a biomarker signal from the bundle of His with the electrode and the fixation element as a bipolar sensing pair.

In example 11, a lead delivery system for delivering a lead to the bundle of His from below the tricuspid valve in the right ventricle, the delivery system comprising: an outer guide catheter having a proximal end, a distal end, a distal tip, a lumen having an opening at the distal tip of the outer guide catheter, and a preformed curve in the distal end of the outer guide catheter, the curve in the distal end of the outer guide catheter approximately 180 degrees, the outer guide catheter configured to be introduced transvascularly and extend down the superior vena cava and position the curve of the outer guide catheter within the right ventricle; and an inner guide catheter having a proximal end, a distal end, a lumen having a opening on the distal end, at least one electrode on the distal end, at least one conductor extending from the electrode to the proximal end, and a curve in the distal end, the inner guide catheter moveable within the lumen of the outer guide catheter and extendable from the opening of the outer guide catheter, the curve in the distal end of the inner guide catheter dimensioned to point the opening of the lumen of the inner guide catheter at a target area immediately below the tricuspid valve in the right ventricle extending 15 millimeters down the septal wall proximate the bundle of His when the curve of the outer guide catheter is within the right ventricle and the curve of the inner guide catheter is extended out of the lumen of the outer guide catheter.

In example 12, the system of example 11, wherein: the outer guide catheter can be rotated at the proximal end to rotate the curve in the distal end of the outer guide catheter about a central axis of the outer guide catheter; and the inner guide catheter is rotatable relative to the outer guide catheter when the curve in the distal end of the inner guide catheter extends past the opening of the outer guide catheter, the curve of the inner guide catheter rotatable along an axis that is not parallel to the central axis of the outer guide catheter.

In example 13, the system of either of example 11 or 12, further comprising an anchor wire having a proximal end, a distal end, and a fixation element on the distal end of the anchor wire, the anchor wire flexible and moveable within the lumen of the inner guide catheter and extendable from the opening of the inner guide catheter, the fixation element configured to penetrate tissue of the target site to anchor the anchor wire to the tissue of the target site.

In example 14, the system of example 13, wherein the anchor wire is configured to be moveable within a lumen of an implantable lead and guide the lead to the target site when the lead is advanced over the anchor wire.

In example 15, the system of example 13, wherein the electrode of the inner guide catheter and the fixation element of the anchor wire are electrically connected to a circuit configured to sense a biomarker signal from the bundle of His with the electrode and the fixation element as a bipolar sensing pair.

In example 16, a method of implanting a lead to stimulate the bundle of His, the method comprising: introducing at least a curve of an outer guide catheter into a right ventricle, the outer guide catheter having a lumen with an opening at a distal tip of the outer guide catheter; extending a curve of an inner guide catheter from the opening of the lumen at the distal tip of the outer guide catheter, the inner guide catheter moveable within the lumen of the outer guide catheter and having a lumen with an opening at a distal tip of the inner guide catheter; extending a fixation element on a distal tip of an anchor wire from the opening on the distal tip of the inner guide catheter, the anchor wire flexible and moveable within the lumen of the inner guide catheter; anchoring the anchor wire to target tissue within the right ventricle by engaging the fixation element with the tissue, the target tissue immediately below the tricuspid valve in the right ventricle and extending about 15 millimeters down the septal wall proximate the bundle of His; and advancing a distal tip of an implantable lead over the anchor wire to the target tissue, the implantable lead having a lumen, the anchor wire within the lumen of the implantable lead during the advancement of the implantable lead.

In example 17, the method of example 16, further comprising locating the target site by sensing a biomarker indicative of the bundle of His with an electrode on the distal tip of the inner guide catheter.

In example 18, the method of example 17, wherein locating the target site further comprises sensing the biomarker by receiving a signal indicative of the biomarker through the fixation element, the biomarker sensed by the fixation element of the anchor wire and the electrode of the inner guide catheter as a bipolar pair.

In example 19, the method of any of examples 16-18, further comprising removing the outer guide catheter and the inner guide catheter from over the anchor wire while leaving the anchor wire attached to the target tissue before advancing the implantable lead over the anchor wire to the target tissue.

In example 20, the method of any of examples 16-19, further comprising rotating the inner guide catheter relative to the outer guide catheter when the curve of the inner guide catheter extends from the opening of the lumen at the distal tip of the outer guide catheter to bring the distal tip of the inner guide catheter in contact with the target tissue.

In example 21, an implantable lead comprising: an anchor wire having a proximal end, a distal end, and a fixation element on the distal end of the anchor wire, the fixation element configured to penetrate tissue to anchor the anchor wire to a target site; an implantable lead having a proximal connector configured to interface with an implantable pulse generator, a distal end, at least one electrode on the distal end of the implantable lead, at least one conductor electrically connected to the at least one electrode and extending to the proximal connector of the implantable lead, and a lumen sized to accommodate the anchor wire, the implantable lead flexible and configured to be advanced over the anchor wire to bring the at least one electrode of the implantable lead in contact with the target site while the anchor wire is anchored to the tissue of the target site and the anchor wire extends within the lumen of the implantable lead; and a terminal pin configured to mechanically connect to the proximal connector and attach the proximal end of the anchor wire to the proximal connector of the lead when the anchor wire is within the lumen of the lead.

In Example 22, the implantable lead of example 21, wherein the terminal pin is configured to be inserted into a proximal opening of the lumen to mechanically connect the terminal pin to the proximal connector.

In Example 23, the implantable lead of example 22, wherein the terminal pin is configured to cause pinching of the anchor wire as the terminal pin is inserted into the proximal opening of the lumen, the pinching of the anchor wire attaching the anchor wire to the proximal connector.

In Example 24, the implantable lead of any of examples 21-23, wherein the terminal pin is configured to electrically connect the anchor wire to an electrical contact.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 is a schematic diagram of an outer guide catheter within the right ventricle according to various aspects of the present disclosure.

FIG. 3 is a schematic diagram of an inner guide catheter extending distally from an outer guide catheter according to various aspects of the present disclosure.

FIG. 4 is a schematic diagram of a fixation element of an anchor wire extending distally from an inner guide catheter according to various aspects of the present disclosure.

FIG. 5 is a schematic diagram of an anchor wire being fixed to target tissue while being supported by guide catheters according to various aspects of the present disclosure.

FIG. 6 is a schematic diagram of an anchor wire fixed to target tissue according to various aspects of the present disclosure.

FIG. 7 is a schematic diagram of an anchor wire guiding a lead to target tissue according to various aspects of the present disclosure.

FIG. 8 is a schematic diagram of a lead being fixed to target tissue according to various aspects of the present disclosure.

FIG. 9 is a schematic diagram of an anchor wire, extending from a guide catheter, fixed to target tissue according to various aspects of the present disclosure.

FIG. 10 is a schematic diagram of an anchor wire, extending from a guide catheter, guiding a lead to target tissue according to various aspects of the present disclosure.

FIG. 11 is a schematic diagram of a lead, extending from a guide catheter, being fixed to target tissue according to various aspects of the present disclosure.

FIG. 12 is an enlarged view a distal tip of a lead, over an anchor wire, being fixed to target tissue according to various aspects of the present disclosure.

FIG. 13 is an enlarged view a distal tip of a lead fixed to target tissue according to various aspects of the present disclosure.

FIG. 14 is a schematic diagram of an anchor wire according to various aspects of the present disclosure.

FIG. 15 is a schematic diagram of an anchor wire according to various aspects of the present disclosure.

FIG. 16 is a schematic diagram of an anchor wire according to various aspects of the present disclosure.

FIG. 17 is cross sectional view of a proximal connector of a lead containing an anchor wire according to various aspects of the present disclosure.

FIG. 18 is a contrived signal trace showing a biomarker indicative of proximity to the bundle of His according to various aspects of the present disclosure.

Figure 1:
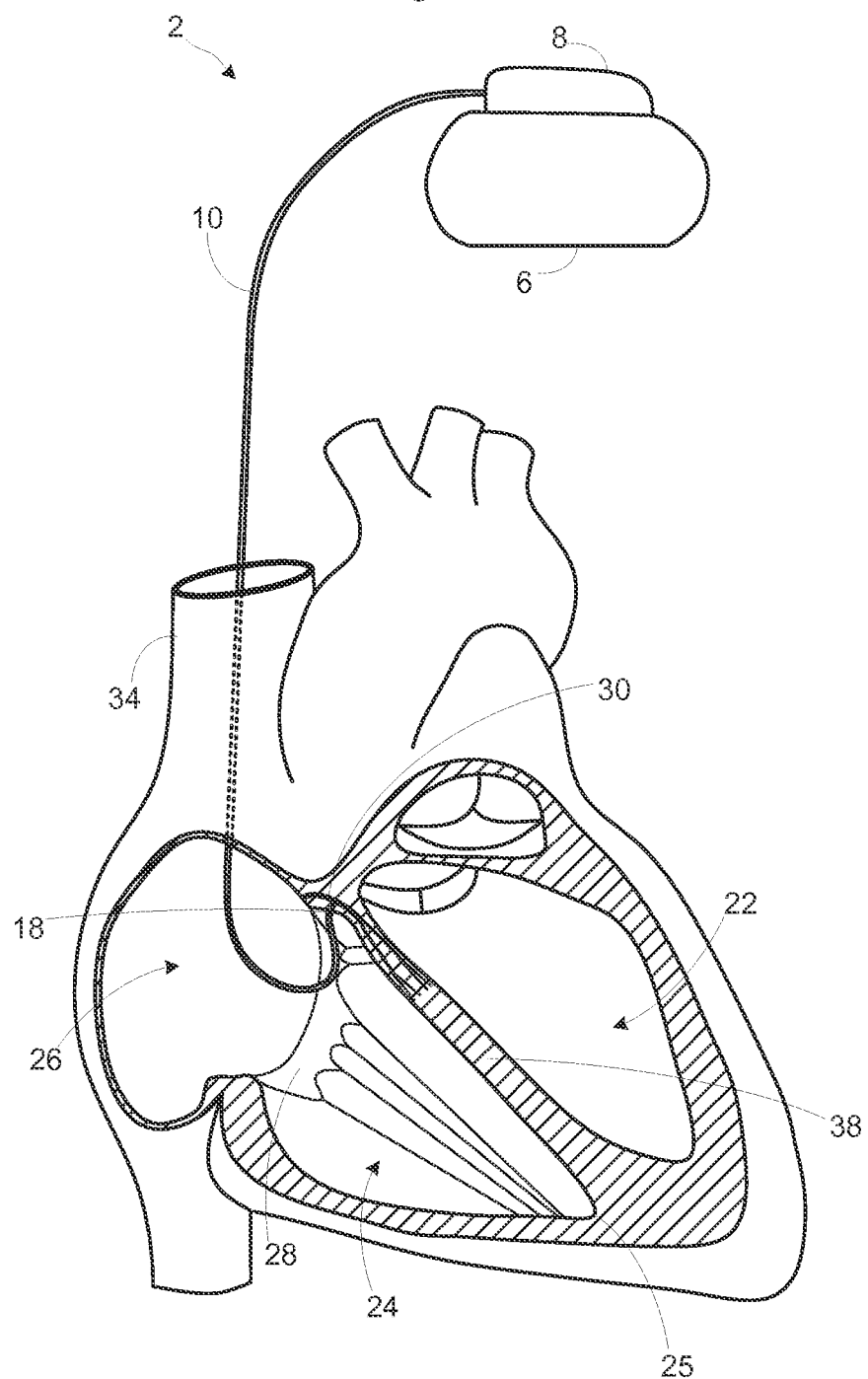
FIG. 1 is a schematic diagram of a His bundle stimulation system including a pulse generator and a lead implanted in a patient's heart according to various aspects of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The output of the heart is dependent on the synchrony of contraction within, and between, the chambers of the heart. Normally, each cardiac cycle is initiated by the depolarization of cells in the sinoatrial node which starts contraction of the cardiac muscle cells of the atria. The electrical impulse continues to the atrioventricular node, which delays propagation of the signal to allow the atria to contract before the ventricles. The distal portion of the atrioventricular node comprises the bundle of His. The bundle of His propagates the depolarization signal to left and right branches in the interventricular septum. The left and right branches propagate the depolarization signal to the left and right ventricles, respectively.

Various conditions can interfere with the normal electrical conduction system of the heart, which can result in arrhythmia and can compromise the output of the heart. For example, conduction block along the atrioventricular node can cause the atria and ventricles to contract out of rhythm. Conventional pacing therapies attempt to bypass the conduction system between the atria and ventricles by implanting a lead in the apex of the right ventricle where, ideally, each pulse delivered to cardiac muscle tissue propagates in a depolarization wave. However, direct stimulation of working myocardium (e.g., at the apex of the right ventricle) can result in slower propagation than direct stimulation of specialized conduction system fibers. For these and other reasons, it can be difficult to replicate the synchronous contractions of a natural conduction system by pacing at the apex of the right ventricle or other working myocardial site alone.

The present disclosure concerns, among other things, using the heart's specialized conduction system by targeting the bundle of His for direct stimulation. In particular, the present disclosure concerns securing one or more electrodes in contact with, or proximate, the nerve fibers of the bundle of His. The bundle of His can be accessed from multiple areas. One area is along the top part of the septal wall in the right ventricle just under the tricuspid valve that separates the right atrium from the right ventricle. However, this area can be a difficult target for lead implantation for several reasons. First, the area is tucked behind the tricuspid valve in what amounts to a corner of the right ventricle. As such, maneuvers to implant a lead at this target site can be awkwardly cramped. Furthermore, the area itself is small and presents a narrow target. Even if the small area is located with a probe sensing a near field biomarker indicating proximity to the bundle of His, it can be difficult to maintain contact with the area while the probe is replaced with a lead and the lead is then affixed to tissue of the area. Finally, the dynamic environment of the beating heart further complicates the process of locating the bundle of His and then stabilizing a lead to stimulate the bundle of His.

Despite the difficulty in implanting a lead at this site, directly stimulating the bundle of His from this location has some particular advantages. For example, in the case of conduction block along the atrioventricular node in the atria or along the proximal portion of the bundle of His, stimulating the bundle of His further down the electrical pathway would be more therapeutically effective at maintaining synchronous contractions. However, if electrical stimulation is directly delivered to nerve tissue too far down the electrical pathway (e.g., halfway down the septum), then the stimulation may be delivered below the bifurcation of the left and right branches that conduct to the left and right ventricles respectively, resulting in only one ventricle being activated by the stimulation. In some embodiments, the target site for implantation of a distal end of a lead for direct stimulation of the bundle of His is immediately below the tricuspid valve in the right ventricle along the septal wall and extends about 15 millimeters down the septal wall away from the tricuspid valve. The present disclosure concerns, among other things, devices, systems, and methods for affixing a lead at this site to directly stimulate the bundle of His.

FIG. 1 illustrates a schematic diagram of a stimulation system 2 for direct stimulation of the bundle of His 30. The stimulation system 2 includes an implantable pulse generator 6. The implantable pulse generator 6 can include circuitry for sensing bioelectrical signals and/or delivering electrical stimulation via one or more leads. The implantable pulse generator 6 can include a lead interface 8 (e.g., a header) for connecting one or more leads to the implantable pulse generator 6. The lead interface 8 can individually connect to respective contacts on the proximal end of the one or more leads, the contacts in respective electrical connection with electrical elements on the distal ends of the one or more leads (e.g., ring electrode, conductive helix) via conductors within the one or more leads.

As shown in FIG. 1, a lead 10 implanted for directly stimulating the bundle of His 30 is connected with the implantable pulse generator 6 through the lead interface 8. The lead 10 operates to convey electrical signals between the bundle of His 30 and the implantable pulse generator 6. In various embodiments, the lead 10 enters the vascular system through a vascular entry site formed in the wall of the left subclavian vein, extends through the left brachiocephalic vein and the superior vena cava 34, traverses the right atrium 26, and is implanted in the right ventricle 24 proximate the bundle of His 30. In other embodiments, the lead 10 may enter the vascular system through the right subclavian vein, the left axillary vein, the left external jugular, the left internal jugular, or the left brachiocephalic vein, for example. Other suitable vascular access sites may be utilized in various other embodiments.

In various embodiments, the lead 10 is a multi-polar medical electrical lead that includes a lead body formed from one or more materials, at least one lumen formed within the lead body, a proximal connector for interfacing with the implantable pulse generator 6, one or more electrical elements (e.g., ring electrodes, conductive helix) on the distal end of the lead 10, and one or more conductors for conducting electrical energy (e.g., bioelectrical signals, stimulation pulses) between the one or more electrical elements and the proximal connector. The lead 10 can have a flexible tubular body having an outer surface. The tubular body can be made from various materials such as silicone rubber and/or polymer material (e.g., polyurethane). In some cases, a distal portion of the lead is more flexible than a proximal portion of the lead. For example, the tubular body and external surface of the distal end of the lead 10, corresponding to a distal portion of the lead within the right ventricle 24 proximate the bundle of His 30, can be less stiff relative to a proximal portion that traverses the tricuspid valve 28 and continues to the lead interface 8. For example, the lead body and external surface of the distal portion can be made from silicone while the lead body and the external surface of the proximal portion can be made from polyurethane to configure the lead to have the distal portion be more flexible than the proximal portion.

The lead 10 can include a fixation element (e.g., a helix) which can fix the lead 10 to cardiac tissue, such as the area of tissue by which the bundle of His 30 can be directly stimulated. The fixation element can be electrically coupled to an electrical conductor (e.g., one or more coils or one or more cable conductors) extending to the proximal end of the lead 10 for interfacing with a channel of the implantable pulse generator 6. As such, a fixation element can mechanically and electrically couple the lead 10 to the tissue and facilitate the transmission of electrical energy from the bundle of His 30 in a sensing mode and to the bundle of His 30 in a stimulation mode.

While the placement of leads at various locations may be able to indirectly stimulate the bundle of His 30, a lead with one or more electrodes in contact with the fibers of the bundle of His, or immediately proximate to the fibers of the bundle of His (e.g., within 5 millimeters), can reliably capture the tissue of the bundle of His 30 (i.e., cause the cells to depolarize and propagate the activation signal) with a pace pulse. For example, an electrode in contact with the bundle of His 30 can capture the bundle of His 30 above the left and right ventricular branches of the specialized conduction system, thereby causing a depolarization wave to travel down the septum 38 along both left and right branches. The depolarization wave can spread to the working myocardial tissue of the left and right ventricles 22 and 24, causing the left and right ventricles 22 and 24 to contract.

While FIG. 1 only shows a single lead connected to the implantable pulse generator 6 and implanted for cardiac stimulation, various other embodiments can have an alternative lead and/or one or more additional leads for sensing bioelectrical activity and/or stimulating the bundle of His 30 or other areas (e.g., the apex of the right ventricle, the left ventricle via the coronary sinus, the right atrium, and/or the left atrium). For example, a His bundle pacing system can be a three lead system having, in addition to the His bundle lead 10, a right ventricular lead with a distal tip fixed to the apex 25 of the right ventricle and a right atrial lead having a distal tip fixed to tissue of the right atrium. The His bundle lead 10 can stimulate the bundle of His 30, and if His capture is not maintained or is unreliable, ventricular capture could also be maintained by the right ventricular lead. The system could be configured such that a pace is delivered to working myocardium of the right ventricle by the right ventricular lead if a lack of contraction is sensed in the right ventricle.

As discussed herein, delivering a lead to a target just below the tricuspid valve within the right ventricle can be a difficult procedure. The small area of tissue that provides access to the bundle of His must first be located. The target can be located by a catheter with an electrode sensing an electrical biomarker indicative of the electrical activation of the bundle of His in a mapping procedure. The biomarker is typically weak and only emerges if the signal is sensed by an electrode proximate the bundle of His (e.g., by sensing the biomarker as a near field signal). In various cases, the one or more electrodes of the mapping catheter will need to be in contact with the tissue that provides access to the bundle of His. Once located by the mapping catheter, a lead must be advanced to the small area. The location of the small area can be lost while the mapping catheter is exchanged for the lead and/or before the lead can be affixed to the small area. However, the devices, systems, and techniques disclosed herein can facilitate the accurate placement and stabilization of a lead at the target location, as shown in FIGS. 2-10.

FIG. 2 is a schematic diagram showing an outer guide catheter 40 according to embodiments of the present disclosure. The outer guide catheter 40 can be a tubular body extruded from polymer material such as, for example, polyamide or polyurethane. The outer guide catheter 40 can include a proximal end 41, a distal end 43, a curve 42 along the distal end 43, and a lumen having a proximal opening and a distal opening 46. The outer guide catheter 40 can be introduced transvensously superior to the heart and advanced down the superior vena cava 34. The distal end 43 can be advanced through the right atrium, through the opening of the tricuspid valve, and into the right ventricle 24. As shown, the curve 42 of the outer guide catheter 40 is within the right ventricle 24, as shown. The proximal end 41 remains outside of the body to allow manipulation of the outer guide catheter 40. As indicated, such manipulation can include axial translation (e.g., advancement and/or retraction) of the outer guide catheter 40 and/or rotation of the outer guide catheter 40. Rotation of the proximal end 41 of the outer guide catheter 40 can rotate the curve 42 about the centerline 44 of the outer guide catheter 40.

A curve in a guide catheter, such as curve 42 in the outer guide catheter 40, can be formed by bending the tubular body to the shape of the curve and then heat setting the tubular body with the curve. While a guide catheter may be flexible, the guide catheter is mechanically biased along the curved section to assume the curved shape. In some embodiments, one or more wires (e.g., a Nitinol wire) can be placed along the curve to structurally support the shape of the curve 42. In some embodiments, the curve 42 of the outer guide catheter 40 curves 180 degrees relative to the centerline 44 (e.g., the centerline 44 being defined by a straight section of the tubular body proximal and adjacent to the curve 42). In some embodiments, the curve 42 is approximately 180 degrees relative to the centerline 44. In some embodiments, the curve 42 is greater than 90 degrees and less than 220 degrees relative to the centerline 44. In some embodiments, the curve 42 is dimensioned to fit within the apex 25 of the right ventricle while pointing the lumen opening 46 at the location of the bundle of His 30 within the right ventricle 24 below the tricuspid valve 28. In some embodiments, the outer guide catheter 40 is configured to brace off of the inner surface of the right ventricle 24, such as the right wall of the right ventricle 24 to face the bundle of His 30. In some embodiments, the outer guide catheter 40 can include a straight section in the tubular body distal of the curve 42.

A lumen can extend the full length of the outer guide catheter 40 and can include an opening 46 on the distal tip of the outer guide catheter 40. A lubricous coating or material may be provided on the inside of the lumen of the outer guide catheter 40 to facilitate the movement of objects within the lumen of the outer guide catheter 40.

In some embodiments, the outer guide catheter 40 can include one or more electrodes. For example, the outer guide catheter 40 as illustrated includes electrode 48. The electrode 48 can be a ring electrode, however other electrode shapes could be provided. The electrode 48 can be located along the outer guide catheter 40 at the apex of the curve 42. The positioning of the electrode 48 at the apex of the curve 42 allows the electrode 48 to make contact with the tissue of the right ventricle 24 when the curve 42 is seated within the apex 25 of the right ventricle 24. The electrode 48 of the outer guide catheter 40 can be exposed on an outer surface of the distal end 43 of the outer guide catheter 40. While one electrode 48 is illustrated on the outer guide catheter 40 in the embodiment of FIG. 2, two or more electrodes can alternatively be placed on the distal end 43 of the outer guide catheter 40. For example, a second electrode could be located on the distal tip of the outer guide catheter 40 adjacent to the lumen opening 46.

An electrode of the outer guide catheter 40, such as electrode 48, can be electrically connected with a respective conductor that extends, within a lumen of the outer guide catheter 40, to a connector on the proximal end 41. The connector can electrically connect with circuitry configured to measure a bioelectrical signal sensed by an electrode. The signal and/or an indicator of a biomarker can be displayed on a screen as part of the circuitry. For example, the proximal end 41 of the outer guide catheter 40 can connect with a pacing system analyzer for sensing cardiac signals and/or delivering stimulation with one or more electrodes of the outer guide catheter 40 or other catheter. Cardiac signals can be sensed by the electrode 48 (or other electrode) in a mapping process to locate particular features in the heart. For example, one or more electrodes of the outer guide catheter 40 (or other catheter) can be moved along cardiac tissue while sensing signals to map the cardiac anatomy based on from where particular signals were received by the one or more electrodes. Target sites for lead implantation, such as the small area of tissue that provides access to the bundle of His 30, can be located by mapping in this manner.

In some embodiments, the outer guide catheter 40 can include a deflection section. The deflection section can be proximal or distal of the curve 42. A deflectable section allows the distal end 43 of the outer guide catheter 40 to be articulated by a mechanism (e.g., a knob, trigger, or lever) on the proximal end 41. The mechanism can place tension on a pull wire attached to the deflection section to cause the deflection section to bend or otherwise move. Such movement can move the distal tip of the outer guide catheter 40.

FIG. 3 is a schematic diagram illustrating, among other things, an inner guide catheter 50. The schematic diagram of FIG. 3 can continue the example of FIG. 2. FIG. 3 shows the introduction of an inner guide catheter 50 through the outer guide catheter 40. The inner guide catheter 50 can be a tubular body with a proximal end 51 and a distal end 53. The inner guide catheter 50 can include features referenced in connection with the outer guide catheter 40. The tubular body of the inner guide catheter 50 can be fabricated in a manner similar to what was described for the outer guide catheter 40. The inner guide catheter 50 can be introduced transvascularly into the heart by being inserted into the proximal opening of the lumen of the outer guide catheter 40 while the outer guide catheter 40 is in the heart until at least a portion of the inner guide catheter 50 extends distally from the lumen opening 46 of the outer guide catheter 40. The inner guide catheter 50 can be longer than the outer guide catheter 40 such that the distal end 53 of the inner guide catheter 50 can extend out of the lumen opening 46 of the outer guide catheter 40 while the proximal end 51 of the inner guide catheter 50 extends proximally from the proximal lumen opening of the outer guide catheter 40, as shown in FIG. 3.

The proximal end 51 of the inner guide catheter 50 remains outside of the body and can be manipulated as indicated to axially translate (e.g., advance and/or retract) the inner guide catheter 50 relative to the outer guide catheter 40. Rotation of the inner guide catheter 50 relative to the outer guide catheter 40 can rotate the distal end curve 52 about the centerline 54 of the inner guide catheter 50. The curve 52 can be formed and supported in the same manner as the curve 42 of the outer guide catheter 40. In some embodiments, the curve 52 curves approximately 90 degrees relative to the centerline 54 (e.g., the centerline 54 being defined by a straight section of the tubular body proximal and adjacent to the curve 52). In some embodiments, the curve 42 curves greater than 70 degrees and less than 110 degrees relative to the centerline 54. In some embodiments, the distal end 53, including the curve 52, is dimensioned to reach an area of the septal wall proximate the bundle of His 30 when the curve 42 of the outer guide catheter 40 is within the right ventricle and the curve 52 of the inner guide catheter 50 extends from the lumen opening 46 of the outer guide catheter 40. The outer guide catheter 40 can further be dimensioned to brace off of one or more walls of the right ventricle to position the lumen opening 46 of the outer guide catheter 40 so that the distal tip of the inner guide catheter 50 can reach the target area of the septal wall proximate the bundle of His 30.

In some embodiments, an inner guide catheter can include one or more electrodes. For example, inner guide catheter 50 can include electrode 56. The electrode 56 can be a ring electrode, however other electrode shapes could be employed. The electrode 56 can be located at the distal tip of the inner guide catheter 50 such that the electrode 56 can receive electrical signals from tissue 36 when the distal tip of the inner guide catheter 50 is in contact with the tissue 36. As such, the distal tip of the inner guide catheter 50 can be moved along the tissue 36 while sensing for a near field biomarker (e.g., a biomarker indicative of proximity to the bundle of His 30). In some embodiments, the distal tip of the inner guide catheter 50 can be moved along the upper part of the septum 38 in the right ventricle 24 while a signal received by the electrode 56 is measured by circuitry for characteristics of the bundle of His 30 (e.g., by a pacing system analyzer as discussed herein). When the biomarker is identified from a sensed signal, it can be determined that the electrode 56 is proximate the bundle of His 30 because the biomarker of the bundle of His 30 is relatively weak compared to the surrounding bioelectrical activity of the rest of the cardiac tissue (e.g., the far field signal indicating atrial depolarization). In some cases, two electrical elements close to one another and the target tissue, sensing as a bipolar pair, can isolate the weak biomarker of the bundle of His 30. Both electrical elements of the bipolar pair may be on the inner guide catheter, distributed between the inner guide catheter 50 and the outer guide catheter 40, or distributed between the inner guide catheter 50 and another member (e.g., an anchor wire, as further discussed herein). Detection of the biomarker indicative of the bundle of His 30 is further discussed in connection with FIG. 18 and elsewhere herein.

While one electrode 56 is illustrated on the inner guide catheter 50 in the embodiment of FIG. 3, two or more electrodes can alternatively be placed on the distal end 53 and/or other part of the inner guide catheter 50. The electrode 56 can be electrically connected with a conductor that extends within a lumen of the inner guide catheter 50 to an electrical connector on the proximal end 51 of the inner guide catheter 50. The proximal end 51 of the inner guide catheter 50 can connect with a pacing system analyzer or other circuitry for sensing cardiac signals with one or more electrodes of the inner guide catheter 50. Cardiac signals can be sensed by the electrode 56 (or other electrode) in a mapping process to locate particular features in the heart. For example, one or more electrodes of the inner guide catheter 50 and/or other catheter can be moved along the surface of cardiac tissue while sensing cardiac signals to map the cardiac anatomy based on from where particular signals are received by the electrode. Target sites for lead implantation, such as the small area of tissue that provides access to the bundle of His 30, can be located by mapping in this manner.

A lumen can extend the full length of the inner guide catheter 50 and can include an opening 58 on the distal tip of the inner guide catheter 50. A lubricous coating or material (e.g., PTFE) may be provided on the inside of the lumen of the inner guide catheter 50 to facilitate the movement of objects within the inner guide catheter 50. An anchor wire 60, as shown in FIG. 4, can be moved through the lumen of the inner guide catheter 50 to extend distally from the lumen opening 58 on the distal tip of the inner guide catheter 50.

In some embodiments, the inner guide catheter 50 can include a deflection section. The deflection section can be proximal or distal of the curve 52. A deflection section allows the distal end 53 of the inner guide catheter to be articulated by a mechanism (e.g., a knob, trigger, or lever) on the proximal end 51. The mechanism can place tension on a pull wire attached to the deflection section to cause the deflection section to bend or otherwise move. Such movement can move the distal tip of the inner guide catheter 50. For example, the electrode 56 and lumen opening 58 can be moved across cardiac tissue (e.g., in a scanning procedure) by actuation of the mechanism to cause deflection of the deflection section.

FIG. 4 is a schematic diagram illustrating, among other things, an anchor wire 60. The schematic diagram of FIG. 4 can continue the example of FIG. 3. The anchor wire 60 can be a solid core, braid, coil, tubular body, or other configuration with a proximal end 61 and a distal end having a fixation element 62. The anchor wire 60 can be fabricated from one or more metal wires, for example. An anchor wire can comprise one or more of a stainless steel wire, a Nitinol wire, a silver wire, a copper wire, or other material. It is noted that the term anchor wire, as used herein, is not necessarily limited to a single wire, and can include various configurations of a single wire or multiple wires. Anchor wires can be solid core wires, braided wires, one or more coiled wires, and/or a combination of these features, among other options.

The anchor wire 60 can be introduced transvascularly into the heart by being inserted into the lumen of the inner guide catheter 50 on the proximal end 51 of the inner guide catheter 50 while the inner guide catheter 50 is within the lumen of the outer guide catheter 40. The anchor wire 60 can be longer than the inner guide catheter 50 and the outer guide catheter 40 such that the fixation element 62 can extend out of and beyond the lumen opening 58 on the distal end 53 of the inner guide catheter 50, as shown in FIG. 4.

In some embodiments, the full length of the anchor wire 60 is coated by an insulative polymer material (e.g., parylene or ePTFE) except for the fixation element 62 and a section on the proximal end 61 to facilitate an electrical connection to circuitry as referenced herein for receiving bioelectrical signals and/or delivering electrical stimulation (e.g., by a pacing system analyzer). In this way, the fixation element 62 can be an electrode for sensing bioelectrical signals and/or delivering stimulation. The anchor wire 60 can be conductive from the fixation element 62 to the proximal end 61. In some cases, an inner conductor wire (e.g., silver or copper) is provided while one or more other materials (e.g., stainless steel, Nitinol) are used to form the outer portions of the anchor wire 60. In some embodiments, the fixation element 62 can connect with the circuitry to be an electrode pair with the electrode 56 on the distal tip of the inner guide catheter 50. The fixation element 62 and the electrode 56 are in proximity to one another (e.g., within 5 millimeters) in the configuration shown in FIG. 4, and can accordingly can be a bipolar sensing pair sensitive to weak near field electrical signals, such as a signal containing a biomarker indicative of the bundle of His 30.

The proximal end 61 of the anchor wire 60 remains outside of the body and can be manipulated as indicated for axial translation (e.g., advancement and/or retraction) and/or rotation of the anchor wire 60 relative to the inner guide catheter 50 and the outer guide catheter 40. Rotation of the anchor wire 60 relative to the inner guide catheter 50 and the outer guide catheter 40 can rotate the fixation element 62 to fix the fixation element 62 to tissue 36. The inner guide catheter 50 can brace the anchor wire 60 to allow the fixation element 62 to penetrate tissue 36. For example, the anchor wire 60 can be braced by the back of the inner lumen wall of the curve 53 of the inner guide catheter 50 so that the activate fixation element 62 can apply enough force to the tissue 36 to penetrate the tissue 36 to access the bundle of His 30. The anchor wire 60 can be configured to have sufficient torsional stiffness to allow as much direct torque transfer as possible between the proximal end 61 and the fixation element 62 to allow penetration of the relatively tough central fibrous body proximate the bundle of His 30 with the fixation element 62. In some embodiments, the anchor wire 60 has as close to infinite torsional stiffness as possible and a torque transfer of about 1:1 such that one turn of the proximal end 61 is transferred to the fixation element 62 with no to minimal attenuation, even when penetrating the fixation element 62 into a tough structure, such as fibrous tissue. An approximate 1:1 torque transfer ratio enables precise control over the fixation process into the fibrous tissue, enabling the physician to stop when the His biomarker is maximized. The fixation element 62 can include a sharpened end to penetrate cardiac tissue and be rigid enough to maintain anchorage to the tissue. The fixation element 62 can be sufficiently long to penetrate through the central fibrous body of the heart tissue 36 and contact the bundle of His 30. In various embodiments, the fixation element 62 is about 2.5 millimeters long. The fixation element 62 can be made out of a conductive metal such that the fixation element 62 can be used for sensing and/or stimulation as well as stabilization of the anchor wire 60. Any fixation element referenced herein can be configured as described above. As shown, a portion of the bundle of His 30 is underneath the cardiac tissue 36. FIG. 5 shows the fixation element 62 having penetrated the tissue 36 to contact the bundle of His 30.

FIG. 5 is a schematic diagram illustrating, among other things, a stabilized anchor wire 60. The schematic diagram of FIG. 5 can continue the example of FIG. 4. FIG. 5 shows that the fixation element 62 has been fixed to tissue 36. As shown, the fixation element 62 is a helix and has been screwed into the tissue 36. As discussed herein, the fixation element 62 can be used for sensing bioelectrical signals indicative of a target, such as the bundle of His 30. Accordingly, a signal can be sensed using the fixation element 62 while the fixation element 62 is advanced into the tissue 36 to assess any changes in signal indicative of the bundle of His 30. For example, a weak biomarker indicative of the bundle of His 30 can be sensed from the surface of the tissue (e.g., by the electrode 58 on the distal tip of the inner guide catheter 50 and/or the fixation element 62 functioning as an electrode), and the signal can become stronger as the fixation element 62 penetrates the tissue 36 and moves closer to the bundle of His 30. The advancement of the fixation element 62 (e.g., where the fixation element 62 is advanced by rotation of the anchor wire 60) can be stopped when the fixation element 62 is in contact with the bundle of His 30 and the fixation between the anchor wire 60 and the tissue 36 is stable. In some cases, the advancement of the fixation element 62 can be stopped when a characteristic of a sensed biomarker indicative of the bundle of His 30 is maximized or crosses the threshold. The maximizing of the characteristic can include the peaking or the leveling out of the amplitude of a morphological biomarker indicative of the bundle of His 30. A threshold can represent satisfactory proximity to, or direct contact with, the bundle of His 30, and advancement of the fixation element 62 can be stopped when a characteristic of a sensed biomarker crosses the threshold. A characteristic of the sensed biomarker that crosses a threshold or in some other way indicates proximity to a target area can be the amplitude of a morphological biomarker.

In some embodiments, the proximity to the bundle of His 30 is assessed by determining to what degree the bundle of His 30 can be captured by electrical stimulation. For example, a pulse may be delivered through an electrical element (e.g., electrode 56 of the inner guide catheter 50 and/or the fixation element 62 of the anchor wire 60). If the pulse fails to capture the bundle of His 30 (e.g., as determined by whether the timing of contraction of the ventricles changes or by QRS morphology changes), then an electrode can be moved to continue mapping and/or a fixation element can be advanced further into tissue. The process can be continued until the delivered pace pulses changes the timing of ventricular contraction, evidencing capture of the bundle of His 30. In some cases, the electrical activation of the bundle of His 30 from a pace pulse can be detected by sensing whether the bundle of His 30 electrically activates following delivery of the pulse. A biomarker for electrical activation of the bundle of His 30 is described herein. The detected electrical activation of the bundle of His 30 can be used to determine when an electrode is properly positioned to capture the bundle of His 30.

When the anchor wire 60 is secured to the tissue 36 and it is determined that the fixation element 62 is close enough to, or in direct contact with, the bundle of His 30, the outer guide catheter 40 and/or the inner guide catheter 50 can be removed while the anchor wire 60 remains attached to the tissue 36. In some cases, the inner guide catheter 50 can be withdrawn first, and the outer guide catheter 40 can be subsequently withdrawn. In some cases, the inner guide catheter 50 and the outer guide catheter 40 can be withdrawn together. In some cases, the inner guide catheter 50 and/or the outer guide catheter 40 can simply be pulled distally over the proximal end 61 of the anchor wire 60. In some embodiments, particularly when an electrical connection is made with the anchor wire 60 for sensing a bioelectrical signal, or a lead is placed over the anchor wire 60, the inner guide catheter 50 and/or the outer guide catheter 40 can have a peel away or splitting feature to allow the inner guide catheter 50 and/or the outer guide catheter 40 to be removed from the anchor wire 60 while being able to leave the anchor wire 60 and any associated electrical and/or mechanical connections in place.

FIG. 6 is a schematic diagram illustrating, among other things, a stabilized anchor wire 60. The schematic diagram of FIG. 6 can be an enlarged sectional view of a portion of the example of FIG. 5. FIG. 6 shows that the inner guide catheter 50 and the outer guide catheter 40 have been withdrawn as described above. The anchor wire 60 remains after the removal of the inner guide catheter 50 and the outer guide catheter 40 because the anchor wire 60 is fixed to the tissue 36 by the fixation element 62. Removal of the inner guide catheter 50 and the outer guide catheter 40 can allow for a lead to be run over the anchor wire 60. In this way, a lead delivery system of the present disclosure allows for accurate location and fixation to a target site before the lead is delivered.

FIG. 7 is a schematic diagram illustrating, among other things, the advancement of a lead 10 over the anchor wire 60. The schematic diagram of FIG. 7 can continue the example of FIG. 6. The lead 10 can be an over-the-wire lead. The lead 10 can include a proximal end 11 which can be manipulated to axially translate (e.g., advance and/or retract) and/or rotate the lead 10. The lead 10 is generally flexible and will follow the anchor wire 60 when advanced over the anchor wire 60. The lead 10 includes a lumen within which the anchor wire 60 can pass as the lead 10 is advanced over the anchor wire 60.

The lead 10 includes a fixation element 16 and an electrode 18. The electrode 18 and the fixation element 16 can be electrically conductive to sense bioelectrical signals and/or deliver electrical stimulation. While one ring electrode 18 is shown, the lead 10 can include a number of ring electrodes (e.g., zero, two, three, four, etc.) and/or other electrical elements (e.g., a defibrillation coil). Each electrical element (e.g., ring electrode, conductive fixation helix) can be electrically connected to respective conductors that run within one or more lumens of the lead to a proximal end connector to electrically connect with respective channels of an implantable pulse generator 6. The fixation element 16 can be a conductive fixation helix that extends from the distal tip 14 of the lead 10 and can function as an electrode (e.g., for sensing and/or delivering stimulation). As shown in FIG. 7, the fixation element 16 can include a lumen within which the anchor wire 60 can run while the lead 10 is advanced over the anchor wire 60. The lead 10 can be advanced until the fixation element 16 makes contact with the tissue 36, which can be detected by greater resistance felt on the proximal end 11 of the lead 10 as the lead is advanced and/or by an electrical signal sensed from the fixation element 16. The lead 10 can be rotated on the proximal end 11 to facilitate advancement of the fixation element 62 into the tissue 36 and fixation of the lead 10.

FIG. 8 is a schematic diagram illustrating, among other things, a stabilized lead 10. The schematic diagram of FIG. 8 can continue the example of FIG. 7. FIG. 8 shows that the fixation element 16 penetrated the tissue 36 and is in contact with the bundle of His 30 to directly stimulate the bundle of His 30 and stabilize the lead 10.

While FIGS. 6-8 show the advancement of a lead 10 over an anchor wire 60 after the inner guide catheter 50 and the outer guide catheter 40 have been removed, either or both of the guide catheters can remain in place during lead 10 delivery. In such cases, the lead 10 can run over the anchor wire 60 while being run though the lumen of a guide catheter (e.g., either of both of inner guide catheter 50 and the outer guide catheter 40) as the lead 10 is advanced to a target site. FIGS. 9-11 illustrate an embodiment that is an alternative to the embodiment of FIGS. 6-8, the embodiment of FIGS. 9-11 leaving the inner guide catheter 50 and the outer guide catheter 40 in the right ventricle, over the anchor wire 60, as the lead 10 is advanced over the anchor wire 60. Specifically, FIG. 9 can continue with the example of FIG. 5, where the anchor wire 60 extends from the lumen opening 58 of the inner guide catheter 50 and is affixed to tissue 36. The lead 10 can be inserted into the proximal opening of the inner guide catheter 50 and advanced within the lumen of the inner guide catheter 50.

FIG. 10 is a schematic diagram which can continue the example of FIG. 9. FIG. 10 shows the lead 10 extending from the lumen opening 58 of the distal end 53 of the inner guide catheter 50. The fixation element 16 of the lead 10 can fit within the lumen of the inner guide catheter 50 in an expanded state (e.g., the size shown in FIG. 10) and the fixation element 16 can be reduced to a smaller size by the inner surface of the lumen of the inner guide catheter 50. In some cases, particularly where the fixation element 16 is compressed within the lumen, space between the tissue 36 and the lumen opening 58 of the inner guide catheter 50 may be left to allow the fixation element 10 to fully assume an unconstrained state outside of the lumen before the fixation element 16 is engaged with the tissue 36 so that proper alignment of the tissue penetrating part of the fixation element 16 with the tissue 36 can be assured. The space left between the tissue 36 and the lumen opening 58 of the inner guide catheter 50 may be greater than the length of the fixation element 16. In some cases, the space left between the tissue 36 and the lumen opening 58 of the inner guide catheter 50 may be slightly greater than the length of the fixation element 16. In some cases, the space left between the tissue 36 and the lumen opening 58 of the inner guide catheter 50 may be approximately equal to the length of the fixation element 16.

The fixation element 16 can be advanced out of the opening 14 of the lumen of the inner guide catheter 50 to engage with the tissue 36 while running over the anchor wire 60. In this way, the anchor wire 60 can continue to guide the lead 10 to the previously identified tissue target while the inner guide catheter 50 can provide support to the lead 10. For example, the lead 10 may be configured for the particular cardiac environment for stimulating the bundle of His 30 from the right ventricle by being particularly flexible, and a guide catheter can provide bracing support to help generate a force at the distal end of the lead 10 sufficient for the fixation element 16 to penetrate the tissue 36. The distal tip of the inner guide catheter 50 may be within a few millimeters of the tissue 36 as the fixation element is advanced to provide bracing support.

FIG. 11 is a schematic diagram which can continue the example of FIG. 10. FIG. 11 shows that the fixation element 16 of the lead 10 has been advanced into the tissue 36 to contact the bundle of His 30. Once the lead 10 is stabilized, one or both guide catheters can be removed. For example, if the inner guide catheter 50 and/or the outer guide catheter 40 are left in place during advancement of the lead 10 over the anchor wire 60, then the inner guide catheter 50 and/or the outer guide catheter 40 can be removed once the lead 10 is affixed to the tissue 36. In some cases, the guide catheters are withdrawn. In some cases, the guide catheters can be peeled or split, as discussed herein, to facilitate the removal of the guide catheters from around the lead 10 and/or other components connected to the lead 10. It is noted that FIGS. 9-11 show the lead 10 being advanced through both the inner guide catheter 50 and the outer guide catheter 40. In other embodiments, the inner guide catheter 50 is removed before advancement of the lead 10 and the lead 10 is advanced within the lumen of the outer guide catheter 40 over the anchor wire 60. In other embodiments, the outer guide catheter 40 is removed before advancement of the lead 10 and the lead 10 is advanced within the lumen of the inner guide catheter 50 over the anchor wire 60. The lead 10 and the lumen of the inner guide catheter 50 and/or the lumen of the outer guide catheter 40 can be dimensioned such that the lead 10 can move within the lumen of the inner guide catheter 50 and/or the lumen of the outer guide catheter 40.

FIG. 12 is a schematic diagram illustrating, among other things, a stabilized lead 10 and anchor wire 60. The schematic diagram of FIG. 12 can be an enlarged sectional view of a portion of the example of FIG. 8 or 11. In particular, FIG. 12 shows a closer view of the fixation element 16 penetrating the tissue 36 and in contact with the bundle of His 30. FIG. 12 also shows that the fixation element 62 of the anchor wire 60 is within the fixation element of the lead 10. Specifically, each of the fixation elements 16 and 62 are helixes and the helix of the anchor wire 16 is coaxial with the helix of the lead 10. The helix of the anchor wire 60 is moveable (e.g., axially translatable and/or rotatable) within the lumen of the helix of the lead 10.

In some embodiments, the anchor wire 60 can be left within the lumen of the lead 10 for chronic implantation. The proximal end 61 of the anchor wire 60, or some other portion of the anchor wire 60, can be connected to the lead 10 and/or the implantable pulse generator 6. In some cases, the lead 10 does not include a fixation element 16 directly attached to the distal tip of the lead 10 and instead relies upon the fixation element 62 of the anchor wire 60 to stabilize the lead 10 for chronic implantation. In such cases, the anchor wire 60 can be attached to the lead 10. Various options for attaching the anchor wire 60 to a lead 10 are further discussed herein.

While some embodiments concern the chronic implantation of the anchor wire 60 to stabilize the lead 10, other embodiments concern the removal of the anchor wire 60 after the lead 10 has been fixed to the tissue 36. In some embodiments, the anchor wire 60 is used temporarily to facilitate the fixation at a target area previously identified in a mapping procedure as providing access to the bundle of His 30. For example, the anchor wire 60 may serve as a tool to locate a small area associated with the bundle of His 30 below the tricuspid valve and then, without losing the location of the target, advance a lead to the area and stabilize the lead for chronic implantation. Accordingly, the anchor wire 60 can be removed following stabilization of the lead 10. FIG. 13 is a schematic diagram continuing with the example of FIG. 12, where the anchor wire 60 has been removed, leaving the lead 10. The fixation element 62 of the anchor wire 60 can be rotated to disengage the fixation element 62 from the tissue 36. The fixation element 62 may be disengaged from the tissue 36 while within the lumen of the fixation element 16 of the lead 10 and while the anchor wire 60 extends through the lumen of the lead 10. In some embodiments where both of the fixation elements 16 and 62 are helixes, the turns of the helixes may be in opposite directions such that the unscrewing of the helix of the anchor wire 60 does not loosen the helix of the lead 10 by frictional engagement between the inner lumen of the lead 10 and the anchor wire 60 rotating in the lumen. For example, the anchor wire 60 may have a clockwise or counterclockwise turning helix while the lead 10 has the other of the clockwise or counterclockwise turning helix.

While the fixation element 62 is illustrated in FIGS. 4-9 as a helix, the fixation element 62 can have a different configuration in various embodiments. FIGS. 14-16 illustrate various anchor wire configurations. FIG. 14 is a schematic diagram of an anchor wire 70 with a fixation element 72. In this case, the main body 71 of the anchor wire 70 is a wire coil and the fixation element 72 is a helix. The anchor wire 70 is made from one or more wires that are wound (e.g., around a mandrel) and heat treated to take the shape of a coil. In some embodiments, one or more uncoiled wires are provided in the lumen of the coiled one or more wires, the one or more uncoiled wires providing additional stability and/or electrical conductivity. The anchor wire 70 can be wound to have a first outer diameter along the main body 71 of the anchor wire 70 (e.g., the section that would span from a proximal end of the anchor wire 70 to the proximal end of the fixation element 72). The one or more anchor wires can further be wound to have an increasing diameter transitioning from the main body 71 to the fixation element 72. The fixation element 72 can be made by winding the one or more wires around a larger part of the mandrel or expanding the distal wire windings after winding. In some embodiments, the orientation of the wire turns along the main body 71 is in the opposite direction as the orientation of the turns of the fixation element 72. For example, the main body 71 may have clockwise or counterclockwise turns while the fixation element has the other of clockwise or counterclockwise turns. Different turn orientations can maintain the integrity of the main body 71 while allowing the helix of the fixation element 72 to be screwed into and/or out of tissue (e.g., the turning does not uncoil the turns of the main body 71). The wires can be insulated along the main body 71 and exposed along the fixation element 72 to allow sensing and/or delivery of electrical energy.

FIG. 15 is a schematic diagram of an anchor wire 74 with a fixation element 76. In this embodiment, the main body 75 of the anchor wire 74 comprises a wire coil and the fixation element 76 comprises a hook. The main body 75 of the anchor wire 74 can be configured in the same way as the main body 71 of the anchor wire 60 of FIG. 14, such as by winding one or more wires to form a coil. The fixation element 76 of the anchor wire 74 can be made from a wire of the main body 75 formed into a hook (e.g., curved and heat set in the shape of a hook). The hook can be advanced from a guide catheter to contact tissue and then turned and/or advanced to penetrate the tissue to stabilize the anchor wire 74 in the tissue.

FIG. 16 is a schematic diagram of an anchor wire 78 with a fixation element 80. In this embodiment, the main body 79 of the anchor wire 78 is formed by a single solid wire. The single solid wire can include an insulator 81. The fixation element 80 of the anchor wire 78 comprises a curve, which can penetrate tissue and then resist removal. In some embodiments of an anchor wire, a fixation element can comprise one or more tines, which may be particularly suitable for chronic implantation of the anchor wire.

FIG. 17 is a schematic diagram of a proximal connector of a lead 82, the proximal connector configured to connect with a lead interface of an implantable pulse generator. The proximal connector of the lead 82 may correspond to the proximal connector of the lead 10 for interfacing with the lead interface 8 of implantable pulse generator 6 of FIG. 1. The proximal connector can comprise a plurality of contacts 84, 88 for electrically connecting with different channels of the implantable pulse generator. Although two contacts 84, 88 are illustrated, a lesser or greater number can be provided in various embodiments, such as a single contact or four contacts. Contact 84 can be a contact ring electrically coupled with conductor 98, the conductor 98 in electrical connection with an electrical element on the distal end of the lead 82.

The lead 82 further includes a terminal pin 86 which can be inserted into the proximal end of the main body of the proximal connector of the lead 82. The terminal pin 86 can mechanically connect the anchor wire 92 to the lead 82. The terminal pin 86 can electrically connect the anchor wire 92 to the contact 88. The main body of the lead 82 can include a lumen 90. The lead 82 can be advanced over the anchor wire 92 as discussed herein, the anchor wire 92 extending within the lumen 90. The terminal pin 86 can further include a lumen 95 inside of which the anchor wire 92 can extend. Once the anchor wire 92 and the lead 82 are stabilized (e.g., fixed to tissue as discussed herein), the length of the anchor wire 92 relative to the lead 82 can then be finalized. The terminal pin 86 can then be fully inserted into the proximal opening of the lumen 90 of the main body of the lead 82. As shown in FIG. 17, the lumen 90 narrows along a proximal section, and the arms 96 of the terminal pin 86 can be forced inward by the narrowing of the lumen 90 to pinch the anchor wire 92 to mechanically connect the anchor wire 92 to the lead 82. In some embodiments, complementary threading is provided within the narrowing portion of the lumen 90 and on the narrowing distal portion of the terminal pin 86 to fix the terminal pin 86 to the main body of the lead 82. The proximal end of the anchor wire 92 can then be cut flush with the proximal terminus of the terminal pin 86. The contact 88 on the terminal pin 86 can be electrically connected with the anchor wire 92 to provide an electrical connection between an exposed portion of the anchor wire 92 (e.g., an uninsulated distal portion of a fixation element in proximity to the bundle of His). As such, a terminal pin or other feature can be provided for mechanically and electrically connecting the proximal end of an anchor wire to the proximal connector of a lead.

FIG. 18 illustrates a contrived signal trace 100 with biomarkers corresponding to sequential events of a cardiac cycle. The sensing of these and/or other biomarkers can be used to identify the bundle of His. In particular, the recognition of one or more biomarkers sensed from one or more electrodes in contact with cardiac tissue during a mapping procedure can be used to determine the location of the one or more electrodes and/or determine whether the one or more electrodes are proximate to a target (e.g., the bundle of His).

The bundle of His is electrically active following atrial depolarization 102 and before ventricular depolarization 106. One or more electrodes can sense a far field atrial depolarization 102 and a subsequent ventricular depolarization 106. If a particular signal feature is not sensed between the atrial depolarization 102 and the subsequent ventricular depolarization 106, then it can be determined that the one or more electrodes are not proximate the bundle of His. The one or more electrodes can be continually repositioned along the cardiac tissue or advanced into the tissue until a bundle of His depolarization 104 associated with the bundle of His is detected between the atrial depolarization 102 and the ventricular depolarization 106. The tissue of the bundle of His is much smaller than the electrically active tissue of either the atria or ventricles. Accordingly, a biomarker signal feature produced by the bundle of His is weak compared to the atrial depolarization 102 and the ventricular depolarization 106. The His bundle depolarization 104 is likely to emerge in the signal trace 100 only when the one or more electrodes are close to the bundle of His (e.g., within 10 millimeters, although this distance may vary between patients). In a mapping procedure, one or more electrodes of a guide catheter (e.g., inner and/or outer guide catheters) and/or a conductive portion of an anchor wire can be moved along the surface of cardiac tissue sensing electrical activity. The emergence of the His bundle depolarization 104 between the atrial depolarization 102 and the ventricular depolarization 106 indicates proximity to the bundle of His, and the surface area along which the one or more electrodes were placed when the emergence was detected can be noted as a target location for accessing the bundle of His. The one or more electrodes can further be moved along the surface of the cardiac tissue until the location that produces the highest amplitude His bundle depolarization 104 is identified. A fixation element of an anchor wire can then be advanced into the tissue of this identified location until the amplitude of the His bundle depolarization 104 peaks or reaches a threshold, which can indicate contact with the bundle of His. A lead can then be implanted at this location by running the lead over the anchor wire to ensure that the lead is implanted at this location. In some embodiments, the bundle of His is identified by delivering electrical stimulation through an electrode (e.g., of an anchor wire or guide catheter) to tissue, and then electrical activity is sensed to determine whether the bundle of His was captured. The location that produces the most reliable capture of the bundle of His can then have a fixation element of the anchor wire engaged with the tissue for delivery of a lead. In some cases, a fixation element can be advanced into the target tissue until pulses delivered through the fixation element capture the bundle of His.

While the use of an anchor wire and other features are discussed in the context of stabilizing a lead to stimulate the bundle of His, the devices, systems, and methods disclosed herein can be adapted to deliver a lead via an anchor wire to other anatomical locations, whether associated with the heart or some other organ. As such, the devices, systems, and methods referenced herein using an anchor wire can be used for delivering a distal tip of a lead to target tissue over the anchor wire. It is further noted that various embodiments can use only one guide catheter (e.g., either the inner guide catheter 50 or the outer guide catheter 40) for securing an anchor wire to tissue of a target site and then advancing a lead over the anchor wire to a target site.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead delivery system for delivering a lead to the bundle of His from below the tricuspid valve in the right ventricle, the delivery system comprising:
    an outer guide catheter having a proximal end, a distal end, a distal tip, a lumen having an opening at the distal tip of the outer guide catheter, and a preformed curve in the distal end of the outer guide catheter, the curve in the distal end of the outer guide catheter approximately 180 degrees, the outer guide catheter configured to be introduced transvascularly and extend down the superior vena cava and position the curve of the outer guide catheter within the right ventricle;
    an inner guide catheter having a proximal end, a distal end, a lumen having a opening on the distal end, at least one electrode on the distal end, at least one conductor extending from the electrode to the proximal end, and a curve in the distal end, the inner guide catheter moveable within the lumen of the outer guide catheter and extendable from the opening of the outer guide catheter, the curve in the distal end of the inner guide catheter dimensioned to point the opening of the lumen of the inner guide catheter at a target site in an area extending from immediately below the tricuspid valve in the right ventricle to about 15 millimeters down the septal wall proximate the bundle of His when the curve of the outer guide catheter is within the right ventricle and the curve of the inner guide catheter is extended out of the lumen of the outer guide catheter;
    an anchor wire having a proximal end, a distal end, and a fixation element on the distal end of the anchor wire, the anchor wire flexible and moveable within the lumen of the inner guide catheter and extendable from the opening of the inner guide catheter, the fixation element configured to penetrate tissue of the target site to anchor the anchor wire to the tissue of the target site,
    wherein the electrode of the inner guide catheter and the fixation element of the anchor wire are electrically connected to a circuit configured to sense a biomarker signal from the bundle of His with the electrode and the fixation element as a bipolar sensing pair.

2. The lead delivery system of claim 1, wherein:
    the outer guide catheter can be rotated at the proximal end to rotate the curve in the distal end of the outer guide catheter about a central axis of the outer guide catheter; and
    the inner guide catheter is rotatable relative to the outer guide catheter when the curve in the distal end of the inner guide catheter extends past the opening of the outer guide catheter, the curve of the inner guide catheter rotatable along an axis that is not parallel to the central axis of the outer guide catheter.

3. The lead delivery system of claim 1, further comprising an implantable lead having a lumen, the anchor wire and the lumen dimensioned such that the implantable lead can be advanced over the anchor wire to the target site.

4. A method of implanting a lead to stimulate the bundle of His, the method comprising:

introducing at least a curve of an outer guide catheter into a right ventricle, the outer guide catheter having a lumen with an opening at a distal tip of the outer guide catheter;

extending a curve of an inner guide catheter from the opening of the lumen at the distal tip of the outer guide catheter, the inner guide catheter moveable within the lumen of the outer guide catheter and having a lumen with an opening at a distal tip of the inner guide catheter;

extending a fixation element on a distal tip of an anchor wire from the opening on the distal tip of the inner guide catheter, the anchor wire flexible and moveable within the lumen of the inner guide catheter;

locating tissue of a target site by sensing a biomarker indicative of the bundle of His, the biomarker sensed by the fixation element of the anchor wire and an electrode on the distal tip of the inner guide catheter as a bipolar pair, the target tissue extending from immediately below the tricuspid valve in the right ventricle to about 15 millimeters down the septal wall proximate the bundle of His;

anchoring the anchor wire to target tissue within the right ventricle by engaging the fixation element with the tissue; and advancing a distal tip of an implantable lead over the anchor wire to the target tissue, the implantable lead having a lumen, the anchor wire within the lumen of the implantable lead during the advancement of the implantable lead.

5. The method of claim 4, further comprising removing the outer guide catheter and the inner guide catheter from over the anchor wire while leaving the anchor wire attached to the target tissue before advancing the implantable lead over the anchor wire to the target tissue.

6. The method of claim 4, further comprising rotating the inner guide catheter relative to the outer guide catheter when the curve of the inner guide catheter extends from the opening of the lumen at the distal tip of the outer guide catheter to bring the distal tip of the inner guide catheter in contact with the target tissue.

* * * * *